(12) United States Patent
Buettner et al.

(10) Patent No.: US 7,847,944 B2
(45) Date of Patent: Dec. 7, 2010

(54) MULTI-PATH FLOW CELL CORRECTION

(75) Inventors: Christian Buettner, Waldbronn (DE); Hubert Kuderer, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 287 days.

(21) Appl. No.: 11/986,403

(22) Filed: Nov. 21, 2007

(65) Prior Publication Data
US 2008/0079942 A1    Apr. 3, 2008

(30) Foreign Application Priority Data
May 24, 2005   (WO) ............... PCT/EP2005/052374

(51) Int. Cl.
G01N 21/00    (2006.01)
(52) U.S. Cl. .................... 356/436; 356/243.1
(58) Field of Classification Search ......... 356/432–440, 356/243.1–243.8, 418–419, 319–320; 250/334, 250/344, 339.12
See application file for complete search history.

(56) References Cited

U.S. PATENT DOCUMENTS

| 2,761,067 | A | * | 8/1956 | Troy, Jr. ............... 250/432 R |
| 4,099,882 | A | * | 7/1978 | Andren et al. ............. 356/411 |
| 5,214,593 | A | | 5/1993 | Magnussen et al. |
| 5,298,978 | A | * | 3/1994 | Curtis et al. ............... 356/627 |
| 5,492,673 | A | * | 2/1996 | Curtis et al. ................. 422/61 |
| 5,602,647 | A | * | 2/1997 | Xu et al. .................... 356/435 |
| 5,689,114 | A | * | 11/1997 | Miyazaki et al. ........... 250/343 |
| 5,859,430 | A | | 1/1999 | Mullins et al. |
| 6,342,948 | B1 | | 1/2002 | Gilby |
| 7,663,755 | B2 | * | 2/2010 | Hafeman et al. ............ 356/436 |

FOREIGN PATENT DOCUMENTS

DE    21 60 836 A1    6/1973

OTHER PUBLICATIONS

International Search Report dated Jan. 18, 2006.

* cited by examiner

*Primary Examiner*—Hoa Q Pham

(57) ABSTRACT

A Method of correcting a multi-path absorbance measuring system is suggested. The multi-path absorbance measuring system has a plurality of n measuring path: The method is executed by correcting the signal of the measuring paths based on a determined linearization function.

14 Claims, 4 Drawing Sheets

US 7,847,944 B2

MULTI-PATH FLOW CELL CORRECTION

This application is the National Stage of International Application No. PCT/EP2005/052374, filed on 24 May 2005 which designated the United States of America, and which international application was published as WO Publication No. WO 2006/125470 which is incorporated by reference in its entirety.

BACKGROUND ART

The present invention relates to multi-path flow cell correction.

Multi-path flow cell systems are known in the art. They are also known as so-called absorbance detectors or flow-through cells such as are commonly used, for example, in high performance liquid chromatography (HPLC). A performance criterion of an absorbance detector is its dynamic range. Mainly two problems are the limiting factors: signal noise and stray light. While noise performance is determined by the light throughput through the sample (or also called analyte), stray light (or more general: false light) is determined by the necessary optics and its components.

Increasing the dynamic range by using multi-path flow cell systems is known in the art. U.S. Pat. No. 6,342,948 B1 (Gilby), for example, discloses a flow cell for absorbance detection with at least two different optical path lengths. A method and accompanying apparatus for automatically extending the linear dynamic absorbance range of absorbance detectors including multi-light path flow cells is disclosed, for example, by U.S. Pat. No. 5,214,593 (Magnussen). The articles "Dynamic Range Improvement in Fourier Transform Infrared Spectrometry", Thomas Hirschfeld, Analytical Chemistry, Volume 50 No. 8, page 1225-1226, July 1978, and the article "Multi-path Cells for Extending Dynamic Range of Optical Absorbance Measurements", Purnendu K. Dasgupta, Analytical Chemistry, Volume 56, page 1401-1403, 1984 disclose the theoretical background of absorbance sensors with more than one flow cell of different path lengths.

DISCLOSURE OF THE INVENTION

It is an object of the invention to provide an improved multi-path absorbance determination. The object is achieved by the independent claims. Preferred embodiments are shown by the dependent claims.

According to embodiments of the present invention, a method of correcting a multi-path absorbance determination system is suggested. The multi-path absorbance determination system can comprises a plurality of n measuring paths. The signal of the measuring paths, in particular the sum of n signals of the n measuring paths, is highly non-linear, but comprises information about the absorbance of a sample within the system, and can be corrected based on values determined for the actual system as the system without the sample. The values can be determined before executing a measurement with the multi-path absorbance determination system. The signal can be corrected based on a linearization function, wherein the linearization function is based on said values. Each measuring path can comprise a cell such as a cuvette or a flow cell.

The idea of the multi-path absorbance determination system is to use at least two paths having significantly different path lengths, for example, lengths ratios up to greater than 100, where the long path determines the signal to noise (S/N) ratio at the lower end of the dynamic range (increased S/N ratio) and the short path length cell determines the upper end of the dynamic range (still enough light at high concentrations, so false light is negligible).

The intensities from the different paths of the cells of the multi-path absorbance determination system can be summed up and afterwards the absorbance calculated from this intensity can be linearized by a linearization function. The linearization function only depends on known parameters, namely the values determined for the actual system, such as the optical path lengths of the different cells and an intensity distribution between the paths at the time when no sample is in the cell.

In a first step, the complete flow cell system or rather all single flow cells of the flow cell system is/are filled with an initial liquid. The initial liquid represents the liquid without the sample/analyte, such as a pure mobile phase as used in HPLC without presence of any sample/analyte. In a second step, the amount of light transmitted through each of the single flow cells of the system is determined for determining the intensity distribution amongst the different paths of the system. Finally, the determined information about the light transmitted through each of the flow cells and the known path lengths of the single flow cells of the system—representing for example said determined values—are used to determine the linearization function for the whole system.

Embodiments may comprise one or more of the following. For determining the intensity distribution amongst the different paths of the system, a signal of a photo detecting device is measured at least n times with appropriate settings of a switching device. Preferably, for each measurement all measuring paths except one can be interrupted by the switching device. On condition of the initial liquid (without presence of any sample/analyte), the measured values represent the intensity distribution amongst the different paths. Under the same premise, but with at least n different patterns of interrupted or non-interrupted measuring paths, the intensity distribution can be determined by establishing a linear system of equations of the form $$A*I=M,$$

wherein "A" is an (m×n) matrix. Each row of the matrix A represents a pattern of one switching state j of the switching device. The variables aij of A can have the values "0" and "1" representing the single switching state for the measuring path j in the switching state i of the switching device with i=[1 ... m] and j=[1 ... n]. A value of aij of "0" represents an interrupted measuring path and a value of "1" represents a non-interrupted measuring path i. "I" is an (n×1) vector representing the amounts of light transmitted through each of the flow cells of the measuring paths j. "M" is an (m×1) vector representing the measured signals (m1 ... mm).

The linear system of equations can be solved (for m>=n), wherein the solution vector I is equal to the intensity distribution amongst the different paths of the system. Preferably, the intensity distribution amongst the plurality of n flow cells is given as follows:

$$fi=I0i/\text{sum}(i=[1 \ldots n]; I0i).$$

For determining the linearization function for the multi-path lengths flow cell system to the response of an equivalent flow cell with a path length of 1 cm, the transfer function for As of the multi-path flow path system can be multiplied with a factor F according to the following equation:

$$A1\text{ cm}=F*As,\text{ with }A1\text{ cm representing the absorbance of a flow cell with a path length of 1 cm.}$$

The transfer function As of the multi-path flow cell system is known from the two aforementioned articles "Dynamic Range Improvement in Fourier Transform Infrared Spectrometry" and "Multi-path Cells for Extending Dynamic Range of Optical Absorbance Measurements":

$$As = -\log(\text{sum}(i=[1 \ldots n]; fi*10^{\wedge}(-pi*A1\,cm))).$$

The combination of the two equations leads to the function for the factor F dependent on the absorbance A1 cm (of the 1 cm flow cell) as follows:

$$F(A1\,cm) = A1\,cm / -\log(\text{sum}(i=[1 \ldots n]; fi*10^{\wedge}(-pi*A1\,cm))),$$

wherein "F(A1 cm)" is the factor used for gaining the linearization function for the measured absorbance, "A1 cm" is the 1 cm absorbance of an equal flow cell with a path length of 1 cm, "As" is the absorbance as measured by the multi-path flow cell system, "fi" is the intensity distribution amongst the different measuring paths i of the flow cell with sum(i=[1 . . . n]; fi)=1, and "pi" is the length of the flow cell i with i=[1 . . . n].

The equation above can be numerically inverted point by point to serve as the linearization function to calculate the absorbance A1 cm as a function of the measured absorption.

Advantageously, the dynamic range of the system can be enhanced additionally by determining the linearization function for different wavelengths of the spectral range of the light emitting device. When executing the methods with a diode array detector, advantageously the whole spectrum is used for quantization and identification. In this case, the measured absorbance of a compound (of the sample) not only has to be within the dynamic range at a certain wavelength, but in the whole wavelength range of interest. As a matter of fact, the allowable concentration range of a certain compound is decreased by the dynamic range of its spectrum, which easily can be a factor of 10 or more compared to a single wavelength measurement. Therefore, especially diode array detectors will benefit from a dynamic range increase.

In theory, the linearization function can be determined numerically. In practice, mainly two conditions are of relevance: The different paths always need to detect identical sample concentrations, and the light distribution amongst the different paths has to be exactly known at the time when no sample is in the cell to determine the correct transfer function for multiple path length cells. Therefore, using multiple path length cells can be made under the assumption, that the two or more paths of the cell contain the same sample concentration at any time.

In particular for optimizing systems with varying sample concentrations, further embodiments of the invention relate to a method of minimizing side effects of a multi-path absorbance determination system, for example, a multi path flow cell system.

In particular for fast LC applications, the sample concentrations and dilution of the sample concentration between the different paths may vary. This effect depends in particular on the geometry of the single flow cells and a respective dead time in fluid conduits to the flow cells. Advantageously, occurring side effects can be minimized as follows: The system can be adapted for measuring the absorbance of a sample and can comprise a plurality of n flow cells with different light-path-lengths pi, with i=[1 . . . n], connected fluidically in series. The side effects relate to the time delay and dilution of the sample concentration between the plurality of n flow cells, the different residence time of the sample within the cells and time-dependent concentration changes of the sample.

In a first step, the individual absorbance signals of the plurality of n flow cells can be detected. In a second step, at least one of the individual absorbance signals can be transformed. Each transformation can comprise a time-shift for compensating the time delay between the plurality of n flow cells, and/or a peak broadening for compensating the dilution of the peak concentration, and/or an inversed peak broadening. Advantageously, the transformation simulates for each reading of the first step a stagnant system without side effects caused by the streaming time-varying sample. Advantageously, the transformed absorbance signals can be used for calculating the related intensities of each of the plurality of n flow cells.

Advantageously, by-products as a percentage of a main compound (of the sample) can be determined. To determine very low percentages of by-products, the concentration of the main compound is increased until it reaches the upper limit of the dynamic range of the detector. Ongoing requests for the determination of lower and lower percentages of by-products can only be mastered by an increased dynamic range of the detector.

Advantageously, the method can be used with fast LC applications. Signal filtering is commonly used to decrease signal noise and therefore leads to a greater dynamic range of the detector. For fast LC applications however, filtering has to be reduced to avoid peak broadening and loss of resolution.

Another typical application is the spectral evaluation of substances. The dynamic range of a detector depends on the measured absorbance but not on the concentration of a compound. To fully exploit the dynamic range of a detector, following parameters may be changed: Sample concentration, injection volume, cell path length or measurement wavelength.

Advantageously, the dynamic range of the multi-path absorbance determination system can be enhanced without the need of a significant increase in light throughput or a significant reduction of false light, which is neither affordable nor feasible. Advantageously, common detectors can be used.

Any additional step for determining the light intensity of the mobile phase prior to any use of the multi-path absorbance determination system may not be necessary.

Advantageously, calculating the absorbance of every path individually before combining the information from the different absorbance signals with the help of a blending function is not necessary.

Other embodiments of the invention relate to a multi-path absorbance determination system comprising multiple path lengths, for example a multi-path length flow cell system, for measuring the absorbance of a sample. The system can comprise a light emitting device for irradiating the sample and a plurality of n measuring paths adapted for conducting the irradiated light through the sample and the ability for separately determining the light intensities of the different paths. For example, the separately determined intensities can be used to determine the light distribution among the different paths at the time, when no sample is in the cell.

Advantageously, the system can comprise a switching device adapted for realizing at least n−1 different switching states for interrupting at least one of the measuring paths of the system in each state. The plurality of n measuring paths of the system can comprise, for example, a plurality of n flow cells, with different light path lengths. The (light) path length of a flow cell can be defined as the length of the light path through the measuring path, for example through a liquid within a flow cell of a measuring path; normally dimensioned in cm. In other words, in each switching state of the switching device, the system, for example the multi-path flow cell system, can be operated with a different number and/or pattern of individual flow cells. The path length of the system can be determined by evaluating the signals generated by the photo detection device of each individual flow cell. Advantageously, the photo detecting device can be adapted for measuring, for example separately, the sum of the light conducted through all of the non-interrupted measuring paths in each switching state of the switching device. Besides this, the photo detecting device can be adapted for measuring the light intensity of each single measuring path, for example concurrently with a plurality of single photo detectors or sequentially with just one common photo detector and sequentially irradiated flow cells.

In one embodiment, the plurality of n different sums of light intensities can be determined, for example by calculating and/or measuring, with the initial liquid and the n different light-path-lengths of the n measuring paths. Advantageously, this delivers necessary information for determining the linearization-function of the multi-path absorbance determination system. For realizing a multi-path system the measuring paths of the system can comprise a plurality of n flow cells or a plurality of n UV/Vis cells, for example cuvettes, test cells, and/or glass cells, each with different light-path-lengths pi with i=[1 ... n] coupled to the light emitting device and to the photo detecting device In one embodiment, each measuring path of the system comprises one flow cell with different path lengths. The measuring paths are optically connected in parallel, while the sample flow through the cell may be in series or in parallel. The signal generated by the photo detection device is proportional to the sum of light intensities conducted by all non-interrupted measuring paths.

For calibrating the system it is important to know the exact intensity distribution amongst the different measuring paths. For determination of this distribution, in particular before each measurement, the plurality of n flow cells of the system has to be filled with the same initial liquid and the signal of all measuring paths are measured with appropriate settings of the switching device. The number of n different signals detected by the photo detection device is used for determining the intensity distribution to the different paths.

In one embodiment, the switching device can be adapted for interrupting one or more light paths through the system and/or one or more electrical paths. For this purpose, the switching device can comprise an aperture, a liquid crystal device, a shutter, a current switch, and/or a software switch. Advantageously, the light-emitting device can comprise just one light source. The light intensity distribution amongst the different paths can be realized by means of an optical system. It may be of advantage to adjust the light distribution through the different paths to realize a certain transfer function.

The light-emitting device can also comprise a plurality of individual light sources for realizing the intensity distribution for each path. Each light source can be coupled with at least one flow cell of the system. The light transmitted through the single flow cells of the system is detected by the photo detecting device. The photo detecting device can comprise a plurality of single photo detectors coupled to the single cells of the system.

In one embodiment, a photo detecting device may comprise one or multiple photo sensors connected to the multi-path flow cell system. Each of the photo sensors can be realized by a photo diode or a photo diode array. It further may comprise a light dispersive element to measure the intensity at various wavelengths.

For reducing the complexity of the system, the photo detecting device and/or the light emitting device can comprise just one single photo detector and just one single light source. The light transmitted through the plurality of n cells of the system can be emitted from the single light source, distributed to the plurality of n measuring paths, and finally directed to just one single photo detector. This can be done, for example, by the light guide, by the optical fiber waveguide, or by a suitable lens system. The single photo detector generates an output signal proportional to the sum of the light transmitted through the plurality of flow cells of the system.

Advantageously, the system can comprise a control unit coupled to at least one element of the plurality of measuring paths. The control unit can be used for controlling the settings of the switching device, for determining the intensity distribution, and for calibrating the system. For calibrating and/or correcting the system, the linearization function is calculated, for example by the control unit, by using known parameters of the system, for example a transfer function, the intensity distribution amongst the different flow cells of the system, and the dimension or rather the length of the different flow cells of the system. The transfer function of a multi-path flow cell system with a known intensity distribution amongst the different measuring paths and the known path length is known in the art and described for example in the two aforementioned articles "Dynamic Range Improvement in Fourier Transform Infrared Spectrometry" and "Multi-path Cells for Extending Dynamic Range of Optical Absorbance Measurements".

The invention can be partly or entirely embodied or supported by one or more suitable software programs, which can be stored on or otherwise provided by any kind of data carrier, and which might be executed in or by any suitable data processing unit. Software programs or routines are preferably applied for controlling the multi-path flow cell system and/or for correcting the system, in particular for determining and/or calculating the linearization function.

BRIEF DESCRIPTION OF DRAWINGS

Other objects and many of the attendant advantages of embodiments of the present invention will be readily appreciated and become better understood by reference to the following more detailed description of preferred embodiments in connection with the accompanied drawing(s). Features that are substantially or functionally equal or similar will be referred to with the same reference sign(s).

FIG. 1 shows a multi-path flow cell system 1 with two measuring paths 3 and 5, a first measuring path 3 and a second measuring path 5. Besides this, the multi-path flow cell system 1 comprises two flow cells 7 and 9, wherein a first flow cell 7 is part of the first measuring path 3 and a second flow cell 9 is part of the second measuring path 5. The first flow cell 7 realizes a light path with the length p1 and a second flow cell 9 realizes a light path with the length p2 each being part of the measuring paths 3 and 5. The flow cells 7 and 9 are connected fluidically in series via a coupling 11. Each of the flow cells 7 and 9 comprises an inlet 13 and an outlet 15 and is adapted for analyzing a continuous flowing liquid. Consequently, the flow cells 7 and 9 of the multi-path flow cell system 1 are realized as flow-through cells or rather flow-through cuvettes. In other embodiments, the flow cells 7 and 9 of the flow cell system 1 are not connected fluidically in series. For this purpose, the plurality of flow cells 7 and 9 can be realized as a plurality of cuvettes as known in the art.

Figure 1:
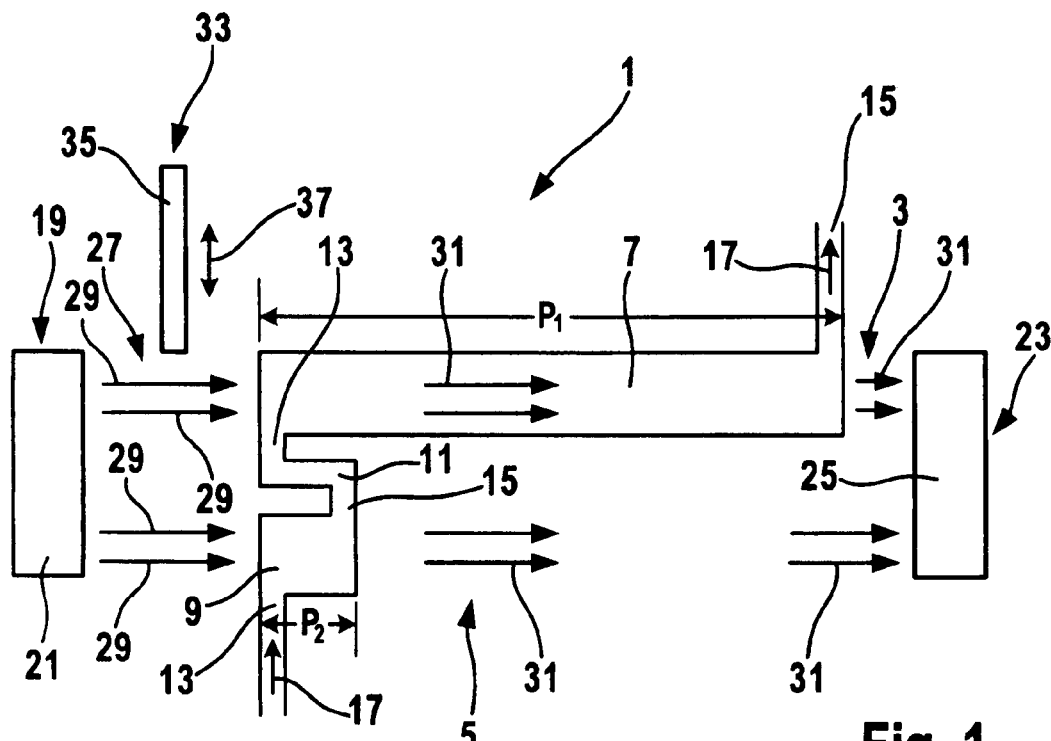
FIG. 1 shows a multi-path flow cell system with a shutter and with two flow cells with different lengths each being part of a measuring path.

The multi-path flow cell system 1 can be provided with a liquid as symbolized with two arrows 17. The liquid can flow to the multi-path flow cell system 1 from the inlet 13 of the second flow cell 9 to the outlet 15 of the first flow cell 7 via the second flow cell 9, via the outlet 15 of the second flow cell 9, via the inlet 13 of the first flow cell 7. The liquid can comprise a mobile phase for transporting an analyte or rather a sample to be detected. The light paths 5 of the measuring paths 3 and 5 go through the liquid within the flow cells 7 and 9. The multi-path flow cell system 1 comprises a light-emitting device 19 with a light source 21.

Beside this, the multi-path flow cell system 1 comprises a photo detecting device 23 with a photo detector 25. The first measuring path 3 comprises the light source 21, the light path within the first flow cell 7 with the length p1 and the photo detector 25 of the photo detecting device 23. The second measuring path 5 comprises the light source 21 of the light emitting device 19, the light path within the second flow cell 9 with the length p2, and the photo detector 25 of the photo detecting device 23. In this embodiment, the light-emitting device 19 of the multi-path flow cell system 1 comprises just one light source emitting a beam 27 as indicated with 4 arrows 29.

The intensity of the beam 27 of the light source 21 of the light-emitting device 19 is distributed to the first flow cell 7 and the second flow cell 9 in parts of 50%. This intensity distribution is indicated each by one pair of two arrows 29. For splitting the beam, the light-emitting device 19 and/or the multi-path flow cell system 1 can comprise any beam splitting device, for example a light guide, an optical fiber wave guide, a lens system, or alike. The intensity of the beam 27 emitted by the light source 21 is attenuated within the flow cells 7 and 9 by the liquid within the flow cells 7 and 9, as indicated with further arrows 31. For producing the intensity distribution amongst the two flow cells 7 and 9 of the multi-path flow cell system 1, the light emitting device 19 can comprise more than one light source. Therefore, for each flow cell 7 and 9 of the multi-path flow cell system 1, the light emitting device 19 can comprise a single light source, for example with different light intensities.

Additionally, the multi-path flow cell system 1 comprises a switching device 33 with a shutter 35. The shutter 35 of the switching device 33 is adapted for interrupting the first measuring path 3 of the multi-path flow cell system 1 or rather for interrupting a part of the beam 27 of the light source 21 of the light-emitting device 19. The said part of the non-interrupted beam 27 of the light source 21—as shown in FIG. 1—hits the first flow cell 7 of the multi-path flow cell system 1.

Figure 2:
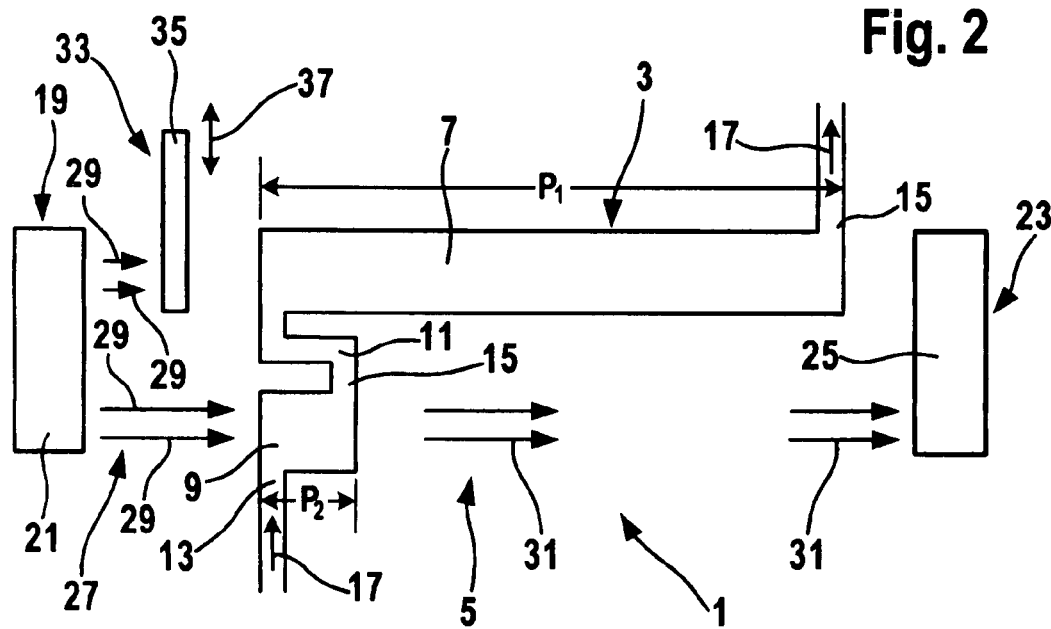
FIG. 2 shows the system of FIG. 1, wherein one measuring path is interrupted by the shutter.

FIG. 2 shows the multi-path flow cell system 1 of FIG. 1, wherein the first measuring path 3 is interrupted by the shutter 35 of the switching device 33. Therefore, the shutter 35 of the switching device 33 can be moved—in direction of FIGS. 1 and 2—up and down, as symbolized with a double arrow 37. Consequently, just the light transmitted through the second flow cell 9 of the multi-path flow cell system 1 can hit the photo detecting device 23. The light path of the first flow call 7 is closed by the shutter 35 of the switching device 33.

For calibrating the multi-path flow cell system 1 as shown in FIGS. 1 and 2, the flow cells 7 and 9 of the system 1 can be filled through the inlet 13 of the second flow cell 9 with an initial liquid, for example with a mobile phase as used for an HPLC without presence of any analyte.

In the switching state of the switching device 33 as shown in FIG. 1, the photo detecting device 23 can detect the complete beam 27 transmitted through the flow cells 7 and 9.

In the switching state of the switching device 33 as shown in FIG. 2, the photo detector 25 of the photo detecting device 23 can detect only the light transmitted through the second flow cell 9. The signal generated by the photo detecting device 23, in the setting as shown in FIG. 2, is equivalent to the intensity of light transmitted through the second flow cell 9.

The difference of the two signals of the photo detecting device generated in the switching state of the switching device 33 as shown in FIG. 1 and generated in the switching state of the switching device 33 as shown in FIG. 2, is equivalent to the intensity of light transmitted through the first flow cell 7.

Under the premise of filling the multi-path flow cell system 1 with an initial liquid, these two values represent the relevant intensity distribution amongst the first measuring path 3 of the first flow cell 7 and the second measuring path 5 of the second flow cell 9 of the multi-path flow cell system 1.

The method of determining the intensity distribution amongst the first measuring path 3 of the first flow cell 7 and the second measuring path 5 of the second flow cell 9 of the multi-path flow cell system 1 as described above can be extended to a multi-path flow cell system with a plurality of n different flow cells.

Figure 3:
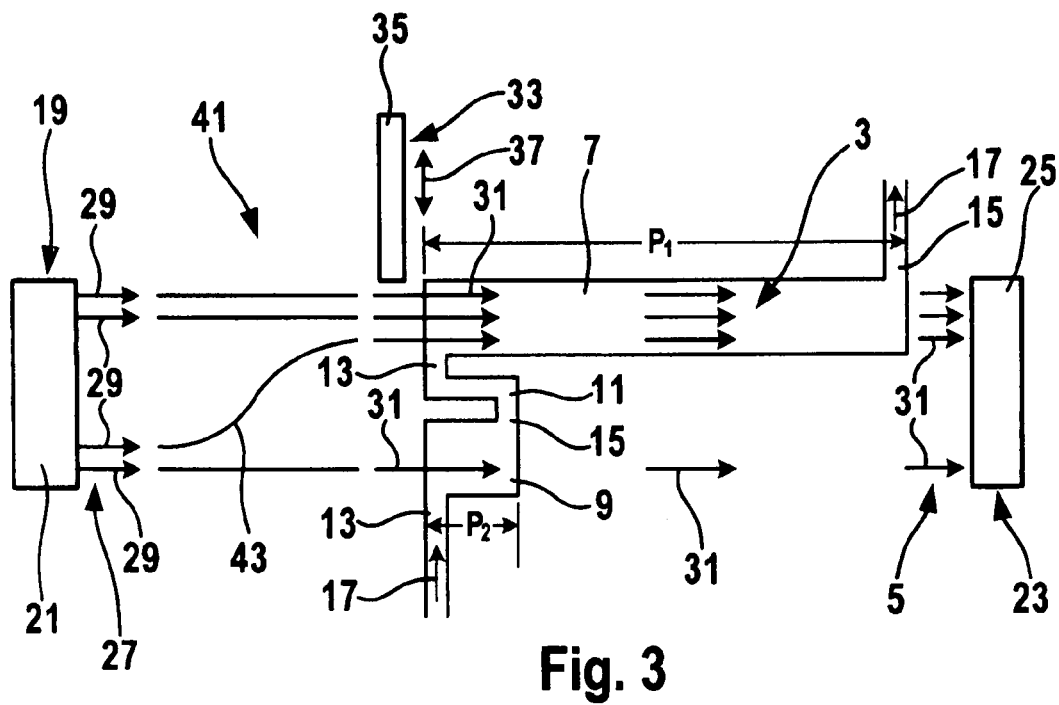
FIG. 3 shows a multi-path flow cell system with a fiber optic and a shutter.

FIG. 3 shows a multi-path flow cell system 39 with a fiber optic 41 comprising an optical fiber waveguide 43. In difference, the intensity distribution between the first measuring path 3 and the second measuring path 5 is influenced or rather determined by the optical fiber waveguide 43. Therefore, a part of the intensity is guided by the optical fiber waveguide 43 towards the first flow cell 7. In this embodiment, the intensity distribution is 75% for the first flow cell 7 to 25% for the second flow cell 9. For measuring this intensity distribution, the shutter 35 of the switching device 33 can be set as described above. The switching device 33 can also be positioned between the end of the first flow cell 7 and the photo detecting device 23. Besides this, the shutter 35 of the switching device 33 can be adapted additionally or alternatively for interrupting the second measuring path 5 and be positioned accordingly.

Figure 4:
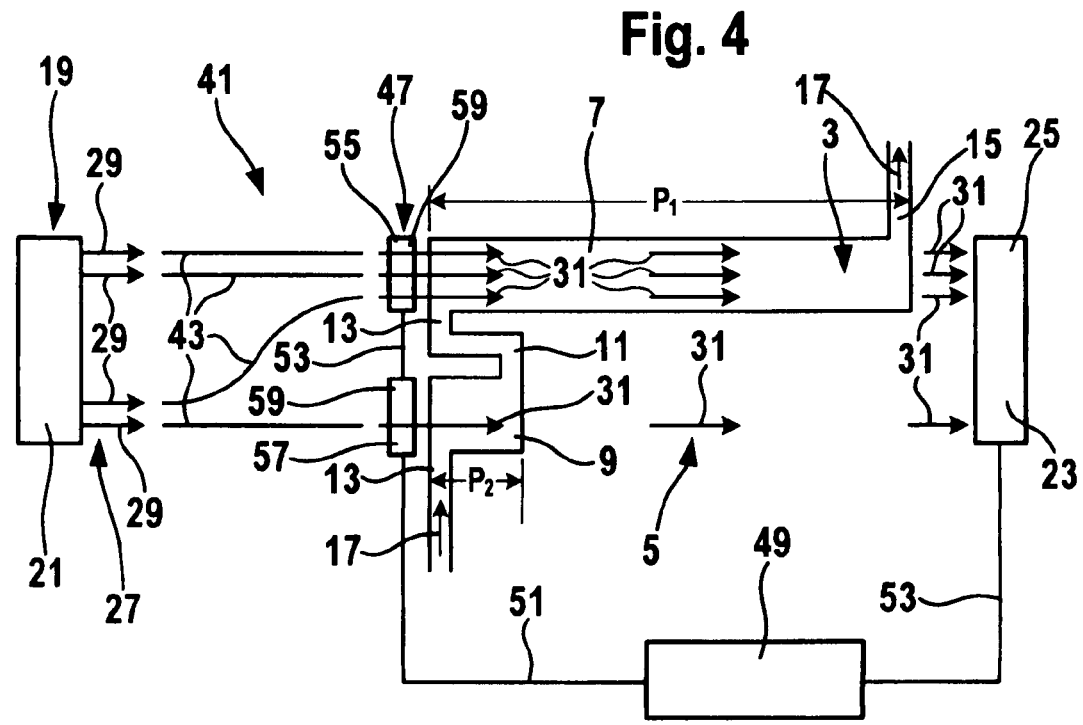
FIG. 4 shows a multi-path flow cell system with a fiber optic and a switching device controlled by a control unit.

FIG. 4 shows a multi-path flow cell system 45. The multi-path flow cell system 45 comprises a switching device 47 and is controlled by a control unit 49. The control unit 49 is connected with the switching device 47 and with the photo detecting device 23 via control lines 51 and 53. For controlling the light emitting device 19, the multi-path flow cell system 45 can additionally comprise a not shown control line between the multi-path flow cell system 45 and the control unit 49. The switching device 47 comprises a first controller 55 and a second controller 57, wherein the first controller 55 is coupled with the first measuring path 3 of the multi-path flow cell system 45 and the second controller 57 is coupled with the second measuring path 5 of the multi-path flow cell system 45.

Each of the controllers 55 and 57 of the switching device 47 comprise an element for interrupting the measuring path of the multi-path flow cell system 45, for example a shutter, an aperture, a liquid crystal device, or alike. In the embodiment as shown in FIG. 4, the controllers 55 and 57 of the switching device 47 comprise a liquid crystal device 59. The liquid crystal device 59 of the controllers 55 and 57 of the switching device 47 can be switched by the control unit 49 from a transmissible setting to an opaque setting.

Figure 5:
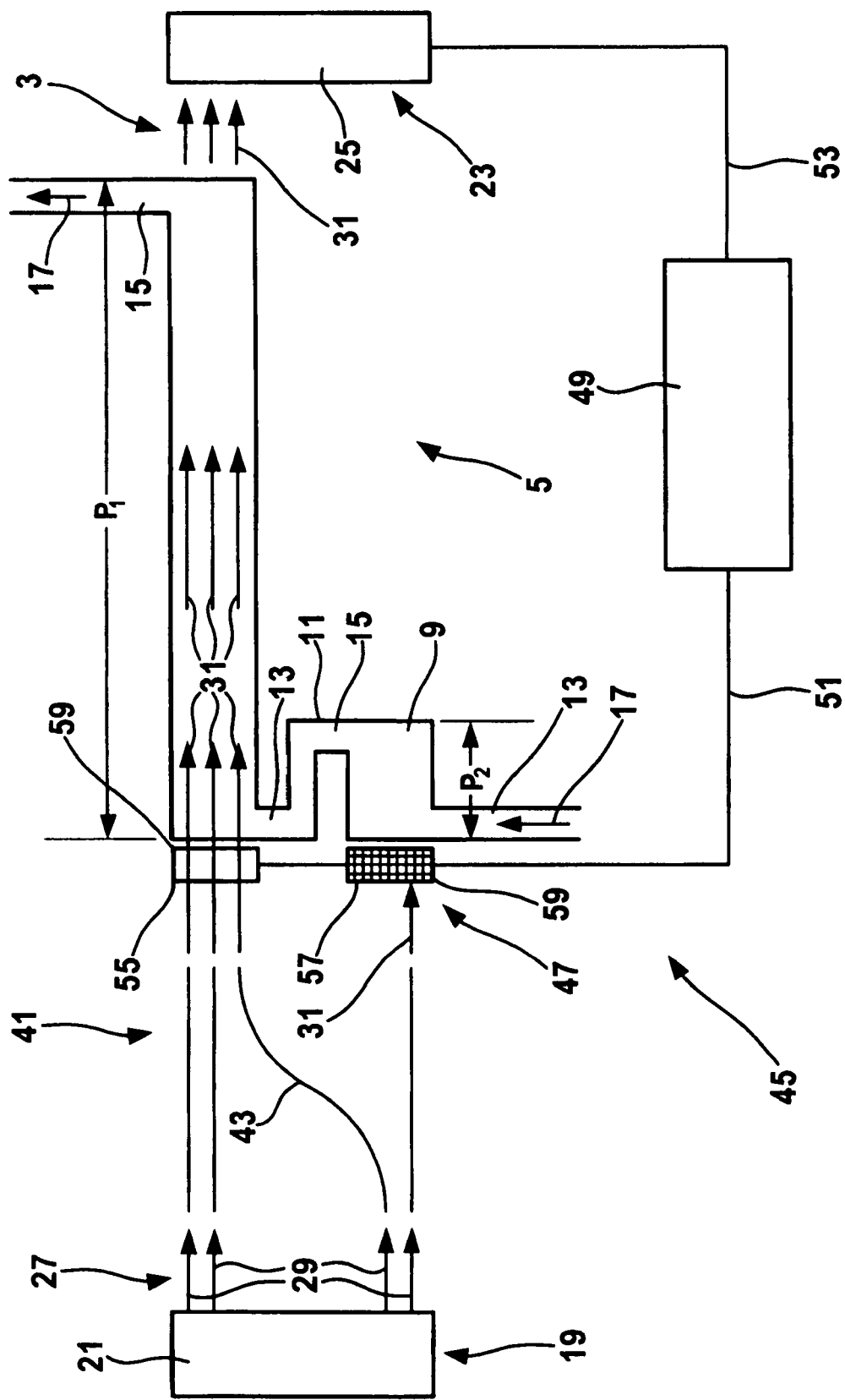
FIG. 5 shows the system of FIG. 4, wherein one measuring path of the multi-path flow cell system is interrupted by the switching device.

FIG. 5 shows the same multi-path flow cell system 45 as shown in FIG. 4, but with another setting of the second controller 57 of the switching device 47, wherein the second controller 57 is opaque. Consequently, in the setting as shown in FIG. 5, the light emitted by the light emitting device 19 cannot pass the second flow cell 9. Consequently, the second measuring path 5 of the multi-path flow cell system 45 is interrupted.

In embodiments, the multi-path flow cell system 45 comprises no switching device 47 for interrupting light paths. Nevertheless, a switching device can be realized by the photo detecting device 23 and/or by the light emitting device 19. Therefore, the photo detecting device 19 can comprise a plurality of photo detectors and/or the light emitting device 19 comprises a plurality of light sources, wherein each measuring path 3 and 5 comprises at least one single photo detector and/or one single light source. In such a configuration, the control unit 49 can read out the single signals of the plurality of photo detectors and/or can control the single light sources. The single signals for each measuring path 3 and 5 can be detected by the plurality of photo detectors or for different switching states of the single light sources, for example controlled by according software and/or software switches. Besides this, the control unit 49 can calculate the intensity distribution amongst the measuring paths 3 and 5 or rather the flow cells 7 and 9 of the multi-path flow cell system 45 out of these single signals.

In the following, a method of calibrating a multi-path flow cell system 1 is described by referring to the figures above:

In a first step, the complete multi-path flow cell system 1 or rather the flow cells 7 and 9 are filled with an initial liquid. For example, the initial liquid is a pure mobile phase, possibly pure water, of a HPLC process without presence of any analyte. In a next step, the amount of light transmitted through each of the flow cells 7 and 9 is determined. Finally, a linearization function for the complete multi-path flow cell system 1 is determined. The intensity distribution over the measuring path 3 and 5 of the multi-path flow cell system 1 can be determined by interrupting at least one of the measuring paths 3 and 5. In total, at least two measurements have to be taken for determining the intensity distribution. For a multi-path flow cell system with a plurality of n different measuring paths, at least n different measurements have to be carried out. Each of the single measurements has to be made with a different setting of the switching device. Besides this, the switching device 33 or 47 has to comprise a setting where no measuring path is interrupted. The n signals measured by the photo detecting device 23 can be inserted in a linear system of equations of the form of $$A*I=M.$$

wherein "A" is a (m×n) matrix, wherein each row of the matrix A represents a pattern of one switching state i of the switching device or rather a (n×n) diagonal with the variables aij with the possible values "0" and "1" representing the single switching state for the measuring path j in the switching state i of the switching device with i=[1 . . . m] and j=[1 . . . n], wherein a value of aij of "0" represents an interrupted measuring path and a value of "1" represents a non-interrupted measuring path j, wherein, "I" is an (n×1) vector representing the amounts of light transmitted through each of the flow cells, and wherein "M" is an (m×1) vector representing the measured signals (m1 . . . mm)

The solution of the linear system of equations gives the intensity distribution amongst the plurality of n flow cells 7 and 9. With the knowledge of the intensity distribution and the individual length p1 . . . pn of all n flow cells 7 and 9 of the multi-path flow cell system 1, a linearization function can be determined by numerically inverting the equation $$A1\,\text{cm}=F(A1\,\text{cm})*As$$

with $$As=-\log(\text{sum}(i=[1\ldots n]; fi*10^{\wedge}(-pi*A1\,\text{cm}))),$$

wherein "F(A1 cm)" is the factor used for gaining the linearization function for the measured absorbance, "A1 cm" is the 1 cm absorbance "c*E" of an equal flow cell with a path length of 1 cm, "As" is the absorbance as measured by the multi-path flow cell system, "fi" is the intensity distribution amongst the different measuring paths i of the flow cell with sum(i=[1 . . . n]; fi)=1, and "pi" is the length of the flow cell I with I=[1 . . . n].

With the values as given in the embodiment of FIG. 1 an 2, with f1=f2=0.5 and pi=[p1, p2] the function to be numerically inverted reduces to $$F(A1\,\text{cm})=A1\,\text{cm}/-\log(2/(10^{\wedge}(-p1*A1\,\text{cm})+10^{\wedge}(-p2*A1\,\text{cm}))),$$

and with p1=5 cm and p2=1 cm to $$F(A1\,\text{cm})=A1\,\text{cm}/-\log(2/(10^{\wedge}(-5*A1\,\text{cm})+10^{\wedge}(-A1\,\text{cm}))),\,\text{with}\,A1\,\text{cm}=c*\epsilon.$$

For realizing an error correction of an error caused by an solvent gradient of solvents used commonly for HPLC processes and/or a rapidly changing concentration of the sample, the measured signal of the shorter flow cell 9 of the second measuring path 5 with the length p2 of the multi-path flow cell system 1, can be measured for multiple times and filtered with an e.g. non-weighted average filter. The average filter can have a window of the integer solution of the proportion p1/p2 of the path lengths. The longer flow cell 7 with the length p1 realizes the same non-weighted average filter, with just one measurement, because of the portion of the gradient being within the longer flow cell 7. Therefore, in the embodiment as shown in FIG. 1, the absorbance of the flow cell 7 can be measured with a time offset.

This makes it possible to measure and filter the same portion of the gradient in both flow cells 7 and 9 of the multi-path flow cell system 1. In the shorter flow cell 9, the portion is measured multiple times and filtered by the average filter. The same portion arrives time shifted in the longer flow cell 7 coupled downstream to the shorter flow cell 9. Consequently, the same portion can be measured with a time delay with the longer flow cell 7. The time delay depends on the different length of the flow cells 7 and 9 and on the volume of a coupling between the flow cells 7 and 9. The same portion has to be measured just once because the length of the light path of the longer flow cell 7 realizes the same average filter as the clock cycled average filter as described above. The sum of the time shifted values gives the error-corrected output of the multi-path flow cell system 1.

Besides this, an error correction can be realized by switching the flow cells 7 and 9 of the multi-path flow cell system 1 fluidically in parallel. For optimizing the correction, the volumetric flow rates v1 and v2 through the flow cells 7 and 9 of the multi-path flow cell system 1 can behave proportional to the path lengths p1 and p2 with p1/p2=v1/v2. Therefore, the volumetric flow rates v1 and v2 can be adjusted with a forcing with different diameters and/or flow resistances or an according flow controller of the multi-path flow cell system 1. By this, all flow cells 7 and 9 of the multi-path flow cell system 1 are always filled with the same portion of the solvent gradient of the HPLC. Consequently, the measured absorbance is largely indifferent to the solvent gradient.

Figure 6:
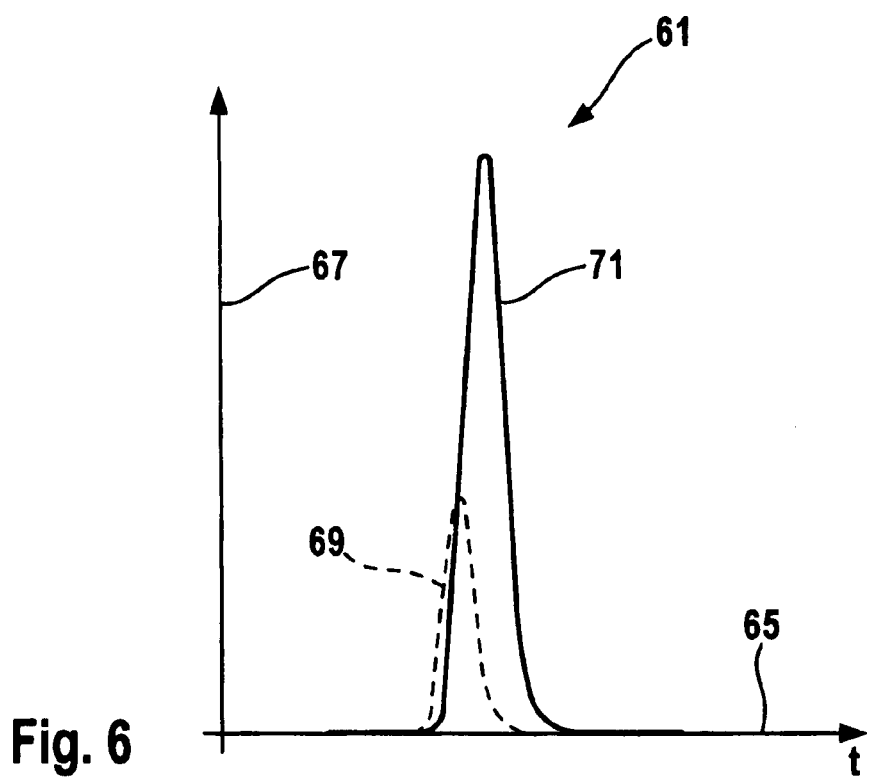
FIG. 6 shows exemplarily a measured value diagram of the determined time-variable absorbance of a short and of a long flow-through cell being connected in series.

FIG. 6 shows exemplarily a first measured value diagram 61 of the determined time-variable absorbance of a flow-through cell comprising a long light path, for example the first flow cell 7 and of a flow-through cell comprising a significantly shorter light path, for example the second flow cell 9, being connected in series.

The shorter flow-through cell is connected upstream of the longer flow-through cell. Consequently, any change of concentration of the sample flowing through the cells reaches firstly the shorter flow cell and is detected firstly. This can lead to undesired side effects and non-correct measured values.

Figure 7:
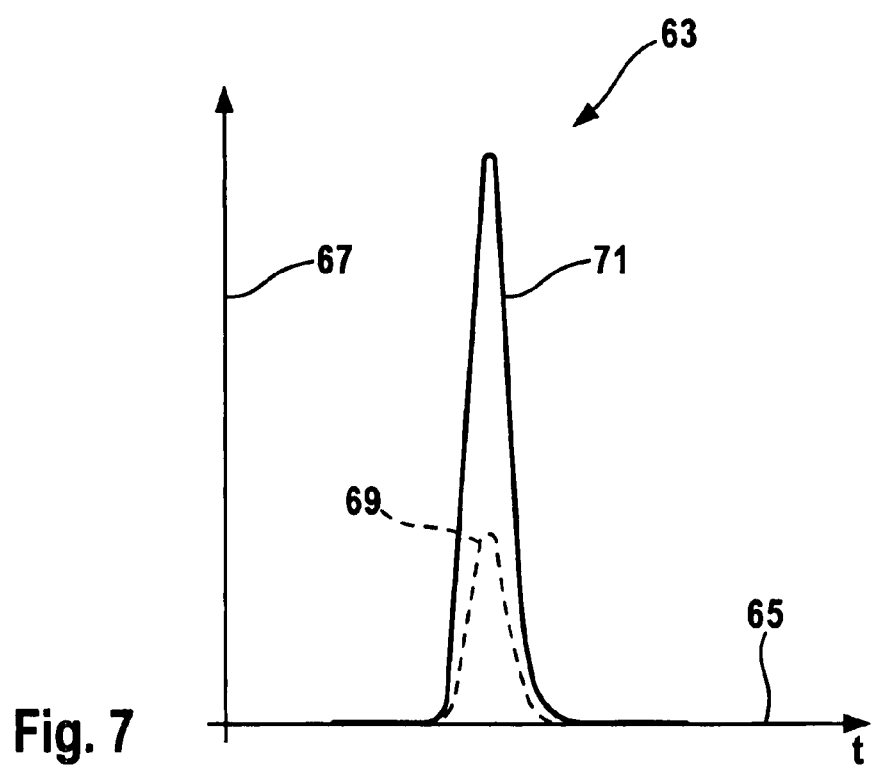
FIG. 7 shows the diagram of FIG. 6, but with transformed measured values by a time-shift and a peak broadening operation.

FIG. 7 shows a second measured value diagram 63, showing the signals as plotted in the first diagram 61, but with transformed measured values by a time-shift and a peak broadening operation for reducing and/or avoiding said side effects.

The diagrams 61 and 63 comprise an x-axis 65 representing the time axis and a y-axis 67 representing the determined absorbance of the first and the second flow cell 7 and 9. The diagrams 61 and 63 show the values exemplarily and not true to scale. Each diagram 61 and 63 shows a dashed chart 69 representing the measured value of the shorter upstream flow cell and a continuous chart 71 representing the measured value of the longer downstream flow cell.

The FIGS. 6 and 7 show the measured values caused by one peak passing the flow cells.

In FIG. 6, the extreme values occur time delayed and comprise a different width. The differences in the width are caused by the differences in the residence time of the peak within the cells caused by the different lengths and, for example same cross section, of the cells.

After transforming the signal of the shorter flow cell as represented by the chart 69 of FIG. 7, the two charts 69 and 71 or better the two peaks differ only by a constant factor, comprising consequently the same width. The transformed signal of the chart 69 of FIG. 7 and consequently the extreme value of the peak is smaller as the original one as shown in FIG. 6.

After transforming the Signal of the shorter flow cell, the related intensities of each of the flow cells based on the transformed absorbance signals can be calculated. Besides this, the transformed signal and the original not transformed signal of the longer flow cell can be used for later steps, for example, for determining a linearization function and/or the resulting absorbance measured by the complete flow cell. Undesired side effects can be avoided by using the values after transforming them as represented in FIG. 7.

In other embodiments, it is possible to map the signal delivered by the longer flow through cell to the signal of the shorter flow through cell. This way leads to a systematic noisier signal, but can make sense if a high resolution per time unit is necessary. Finally, it is possible to transform both signals as described above. The signals can be map to each other resulting also in two signals differing from each other only in a constant factor and consequently usable for reducing undesired side effects and later steps of the measuring chain.

In other embodiments, the diffusion within the cells can be compensated by transforming the signals of the charts 69 and 71 of FIG. 6. Therefore a term can be added to the transforming filter used for the transformation as described above.

In further embodiments, the linearization function can be determined for different wavelengths of the spectral range of the light emitting device. Advantageously, the dynamic range can be enhanced.

Finally, in embodiments, the weighting of the intensity of light irradiated to each of the single flow cells of the system can be varied for influencing the determined linearization function, in particular for moving a discontinuity of the function. The same effect can be achieved by transforming the intensities numerical.

The multi-path flow cell system is adapted for analyzing liquid. More specifically, the multi-path flow cell system is adapted for executing at least one microfluidic process, for example a liquid chromatographic process, for example a high performance liquid chromatographic process (HPLC). Therefore, the multi-path flow cell system can be coupled to a microfluidic device and/or to a liquid delivery system, in particular a pump. For analyzing liquid or rather one or more components within the liquid, the multi-path flow cell system can realize a detection area for the microfluidic device. Otherwise, the multi-path flow cell system can be coupled to a laboratory apparatus, for example a mass spectrometer, for analyzing the liquid. Besides this, the multi-path flow cell system can be a component part of a laboratory arrangement.

It is to be understood that this invention is not limited to the particular component parts of the devices described or to process steps of the methods described as such devices and methods may vary. It is also to be understood, that the terminology used herein is for the purposes of describing particular embodiments only and it is not intended to be limiting. It must be noted that, as used in the specification and the appended claims, the singular forms of "a", "an", and "the" include plural referents until the context clearly dictates otherwise. Thus, for example, the reference to "a light path" or "a measuring path" includes two or more such functional elements.

The invention claimed is:

1. Method of correcting a multi-path absorbance determination system adapted for determining absorbance of a sample contained in a fluid, wherein the multi-path absorbance determination system comprises a plurality of n measuring paths each adapted for measuring an amounts of light transmitted through the-fluid in the measuring path, the method comprising:
   correcting a signal related to the amounts of light transmitted through the fluid in the measuring paths based on correction values determined for the actual system, and
   determining absorbance from the corrected signal,
   wherein the correction values have been determined by:
      filling the measuring paths with an initial fluid as the fluid without containing the sample,
      determining values related to the amounts of light transmitted through the initial fluid in each of the measuring paths, and
      determining the correction values based on the determined values.

2. Method of claim 1, wherein
   correcting the signal of the measuring paths comprises using a linearization function determined from the correction values.

3. Method of claim 2, wherein each measuring path comprises a flow cell, the method comprising
determining a linearization function A1 cm=F*As by
determining an intensity distribution fi with i=[1 . . . n] amongst a plurality of n flow cells, wherein fi=10i/ sum [i=[1 . . . n]; 10i],
inserting the values of fi and pi in the equation $$F[A1\ cm]=A1\ cm/-\log\ [\text{sum}[i=[1\ \ldots\ n]; fi*10^{-pi*A1\ cm}]], \text{ and}$$

inverting the equation numerically point by point for all possible A1 cm within the dynamic range of the multi-path absorbance determination system,
wherein "F[A1 cm]" is the linearization factor dependent on A1 cm, "A1 cm" is the 1 cm absorbance $c*\epsilon$, "As" is the absorbance as a function of the measured absorption of the plurality of n measuring paths by the photo detecting device, "fi" is the intensity distribution amongst the n different measuring paths of the multi-path absorbance determination system for 1=[1 . . . n], and "pi" is the path length of the flow cell i of the multi-path absorbance determination system for 1=[1 . . . n].

4. Method of claim 2, wherein
the linearization function is determined for different wavelengths of the spectral range of the light emitting device.

5. Method of claim 1, wherein each measuring path comprises a flow cell, the method comprising:
setting a switching device to at least n different switching states,
wherein a different pattern of measuring paths is interrupted in each switching state,
measuring the signal of a photo detecting device in each switching state, and
establishing a linear system of equations A*I=M,
wherein A is an m×n matrix, each row of A represents a pattern of values "0" and "1" representing a switching state of the switching device for the plurality of n measuring paths, a value of "0" represents an interrupted measuring path and a value of "1" represents a non-interrupted measuring path, I is an n×1 vector representing the amount of light transmitted through each of the flow cell of the multi-path absorbance determination system, and M is an m×1 vector representing the measured signals of the photo detecting device.

6. Method of claim 1, wherein the multi-path absorbance determination system comprises a plurality of n flow cells with different light-path-lengths pi with i=[1 . . . n] connected in series, and side effects depend in particular on the geometry of the flow cells and a respective dead time in fluid conduits to the flow cells, the method comprising:
detecting individual absorbance signals of the plurality of n flow cells,
transforming at least one of the individual absorbance signals, wherein the transformation comprises at least one of: a time-shift for compensating the time delay between the plurality of n flow cells, a peak broadening, a peak broadening inverse function for compensating the different light-path-lengths, and a term for compensating the diffusion within the cells.

7. Method of claim 6, comprising of:
calculating the related intensities of each of the plurality of n flow cells based on the transformed absorbance signal.

8. A multi-path absorbance determination system for determining absorbance of a sample and for executing the method of claim 1, comprising
a light emitting device for irradiating the sample,
a plurality of n measuring paths for conducting the irradiated light through the sample,
wherein the n measuring paths comprise n different light-path-lengths pi with i=[1 . . . n] and wherein the n measuring paths are coupled to the light emitting device,
a photo detecting device for detecting light emitted by the light emitting device and conducted through the sample by the measuring paths, and
a switching device adapted for interrupting at least one of the measuring paths.

9. The multi-path absorbance determination system of claim 8, wherein the switching device is adapted for realizing at least n−1 different switching states for interrupting at least one of the measuring paths in each state, and for realizing one switching state wherein all measuring paths are non-interrupted.

10. The multi-path absorbance determination system of claim 8, wherein the photo detecting device is adapted for at least one of:
measuring the sum of the light conducted through all of the non-interrupted measuring paths in each switching state of the switching device;
measuring separately a plurality of n different sums of light intensities conducted through all of the non-interrupted measuring paths respectively in the n different switching states of the switching device.

11. The multi-path absorbance determination system of claim 8, wherein the photo detecting device and the switching device are adapted for measuring the light intensity of each single measuring path.

12. A software program or product, stored on a computer readable medium, for controlling the multi-path absorbance determination system of claim 11, when run on a data processing system.

13. The multi-path absorbance determination system of claim 8, wherein the switching device comprises at least one of the following:
an aperture,
a liquid crystal device,
a shutter.

14. A software program or product, stored on a computer readable medium, for executing or controlling the method of claim 1, when run on a data processing system.

* * * * *

UNITED STATES PATENT AND TRADEMARK OFFICE
CERTIFICATE OF CORRECTION

| | | |
|---|---|---|
| PATENT NO. | : 7,847,944 B2 | Page 1 of 1 |
| APPLICATION NO. | : 11/986403 | |
| DATED | : December 7, 2010 | |
| INVENTOR(S) | : Christian Buettner et al. | |

It is certified that error appears in the above-identified patent and that said Letters Patent is hereby corrected as shown below:

On the Title page, in field (57), under "Abstract", in column 2, line 1, delete "A Method" and insert -- A method --, therefor.

In column 12, line 48, in Claim 1, delete "amounts" and insert -- amount --, therefor.

In column 12, line 49, in Claim 1, delete "the-fluid" and insert -- fluid --, therefor.

In column 12, line 51, in Claim 1, delete "amounts" and insert -- amount --, therefor.

In column 14, line 5, in Claim 7, delete "comprising of:" and insert -- comprising: --, therefor.

In column 14, line 7, in Claim 7, delete "signal." and insert -- signals. --, therefor.

Signed and Sealed this
Nineteenth Day of April, 2011

David J. Kappos
*Director of the United States Patent and Trademark Office*